United States Patent

Coombs

(10) Patent No.: US 7,483,516 B2
(45) Date of Patent: Jan. 27, 2009

(54) X-RAY HANDSWITCH APPARATUS AND SYSTEM

(75) Inventor: Kevin Andrew Coombs, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 184 days.

(21) Appl. No.: 11/535,090

(22) Filed: Sep. 26, 2006

(65) Prior Publication Data

US 2008/0075233 A1    Mar. 27, 2008

(51) Int. Cl.
*H05G 1/00* (2006.01)
(52) U.S. Cl. ........................ 378/114; 378/205
(58) Field of Classification Search ......... 378/114–117, 378/205
See application file for complete search history.

(56) References Cited

U.S. PATENT DOCUMENTS

2005/0084071 A1    4/2005    Roos et al.

FOREIGN PATENT DOCUMENTS

EP    0923275 A2  *   2/1998
EP    0923275 A2       6/1999

* cited by examiner

*Primary Examiner*—Hoon Song
(74) *Attorney, Agent, or Firm*—Cantor Colburn LLP

(57) ABSTRACT

A handswitch configured to be held by an operator of an x-ray system, configured for using handswitchable equipment to operate the x-ray system, is disclosed. The handswitch includes an exterior housing so dimensioned as to fit into a hand of the operator. An exposure switch is disposed on the exterior housing and is configured to initiate an x-ray exposure. A tactile feedback mechanism is configured to indicate, to the operator of the x-ray system, transmission of x-rays by the x-ray system.

20 Claims, 2 Drawing Sheets

X-RAY HANDSWITCH APPARATUS AND SYSTEM

BACKGROUND OF THE INVENTION

The present disclosure relates generally to x-ray handswitches, and particularly to handswitch indication of x-ray system status.

Medical environments, such as hospitals, include devices that generate audio tones. An x-ray system relies on a tone and a light to indicate that an x-ray exposure is in progress. The exposure switch, or handswitch, is often attached to a cord, which is in signal communication with a control console of the x-ray system. This allows an operator to step out of the examination room, to avoid being exposed to any of the x-ray radiation. It is thus possible for the operator to be out of sight and hearing range of the exposure indicators that may be located with the x-ray system. Depending on the distance to the console of the x-ray system, the specific tone that relates to the exposure of a particular x-ray system may be difficult to distinguish, particularly in an environment, such as a hospital, that includes other devices that generate audio tones. If the operator does not understand that the exposure has occurred, he or she may decide to re-take the exam, which is undesirable and could potentially result in an image that does not conform to expectations.

When making an x-ray exposure, it is commonly practiced to have an audible indication that an exposure has occurred, such as following activation of an exposure switch on the equipment. This is often accomplished with a tone generator located at an x-ray console. A difficulty often arises, however, because an operator commonly makes the exposure from a remote location, using the handswitch. A noisy environment that has other pieces of equipment that may be generating tones may lead to uncertainty of the operator regarding whether the tone has been generated by the x-ray system to indicate that an exposure has occurred, or if the tone has been generated by other equipment within the environment.

Since it is good practice for the operator to stand as far as possible from the x-ray machine when making an exposure, an attempt to resolve the audibility problem by making the tone louder can result in generation of the tone that is objectionably loud to the subject, as well as to the operator when it is necessary for the operator to attend the subject while making the exposure. Further, an increase in the volume of the tone will only accentuate the ambient noise level of the environment in which the x-ray system is used.

This situation is often compounded because the exposure switch is often operated in series with a prepare switch that commands the x-ray console to prepare the x-ray machine for the expose command, provided in response to activation of the exposure switch. The prepare switch is configured to bring an x-ray tube rotor within the x-ray machine up to speed, so that an x-ray can be generated in immediate response to the activation of the exposure switch. It is often necessary to push and hold the prepare switch while preparing the subject into an optimum position, and then pressing the exposure switch. Holding of the prepare switch can be from a couple of seconds up to about a minute. Other than the sound of the rotor and a display, which can be difficult to distinguish in a noisy environment, or to see when far from the x-ray machine, there is no indication to the operator that the appropriate prepare status has been achieved.

Accordingly, there is a need in the art for an x-ray handswitch arrangement that overcomes these drawbacks.

BRIEF DESCRIPTION OF THE INVENTION

An embodiment of the invention includes a handswitch configured to be held by an operator of an x-ray system configured for using handswitchable equipment to operate the x-ray system. The handswitch includes an exterior housing so dimensioned as to fit into a hand of the operator. The exposure switch is disposed on the exterior housing and is configured to initiate an x-ray exposure. A tactile feedback mechanism is configured to indicate, to the operator of the x-ray system, transmission of x-rays by the x-ray system.

Another embodiment of the invention includes an x-ray system to provide x-ray images of a subject. The x-ray system includes an x-ray machine configured to transmit x-ray radiation and receive the transmitted x-ray radiation having passed through the subject, an x-ray console in signal communication with the x-ray machine, the x-ray console configured to control the x-ray machine, and a handswitch in signal communication with the x-ray console, the handswitch configured to be held by an operator of the x-ray system. The handswitch includes an exterior housing so dimensioned as to fit into a hand of the operator, an exposure switch disposed on the exterior housing configured to initiate the x-ray transmission, and a tactile feedback mechanism configured to indicate transmission of x-rays by the x-ray system to the operator of the x-ray system.

BRIEF DESCRIPTION OF THE DRAWINGS

Referring to the exemplary drawings wherein like elements are numbered alike in the accompanying Figures.

DETAILED DESCRIPTION OF THE INVENTION

An embodiment of the invention provides a tactile feedback mechanism such as vibration, texture changes, or other electro-mechanical mechanism to the exposure command mechanism, also herein referred to as a handswitch. In an embodiment, the feedback can be one of continuous, pulsed, and coded, to indicate edges, or parameters of the exposure.

Figure 1:
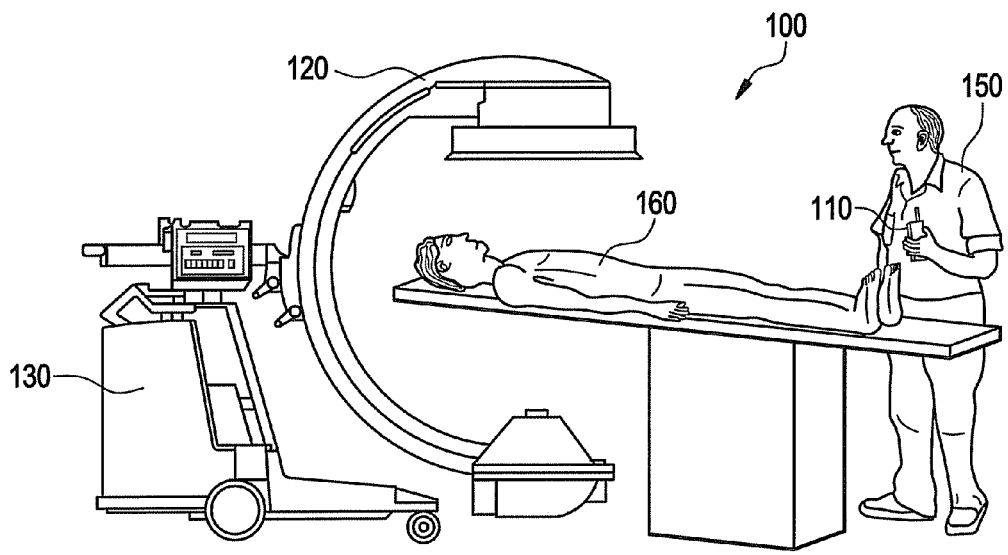
FIG. 1 depicts a perspective view of an exemplary x-ray system in accordance with an embodiment of the invention.

Referring now to FIG. 1, an exemplary embodiment of an x-ray system 100 is depicted. An x-ray machine 120 is configured to transmit x-ray radiation and receive the transmitted x-ray radiation having passed through a subject 160. An operator's x-ray console 130 is in signal communication with the x-ray machine 120, the console 130 being configured to control the x-ray machine 120 and interpret the received x-ray radiation to provide at least one x-ray image. A handswitch 110 is in signal communication with the console 130 via one of a switch cord and a wireless connection, and is configured to communicate with the console 130 to prepare the x-ray machine 120 to take an x-ray exposure. The handswitch 110 is also configured to communicate with the console 130 to initiate the x-ray exposure by the x-ray machine 120. In an embodiment, the handswitch 110 is configured to be held by an operator 150 of the x-ray system 100. In an embodiment, the handswitch 110 is in signal communication with the x-ray console 130 via a wireless connection.

While an embodiment of the invention has been described having a handswitch in signal communication in conjunction with an x-ray machine, it will be appreciated that the scope of the invention is not so limited, and that the invention will also apply to other medical systems that may use handswitches, such as magnetic resonance imaging, and computer aided tomography systems, for example.

Figure 2:
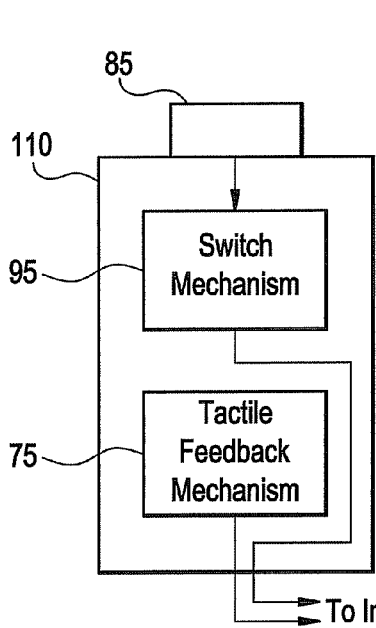
FIG. 2 depicts a pictorial schematic view of an x-ray handswitch in accordance with an embodiment of the invention.

Referring now to FIG. 2, an embodiment of the handswitch 110 is depicted. The handswitch 110 includes a tactile feedback mechanism 75, a push button 85, and a switch mechanism 95. In an embodiment, the push button 85, via the switch mechanism 95, is configured to initiate the x-ray exposure, or provide the expose command to the console 130.

Figure 3:
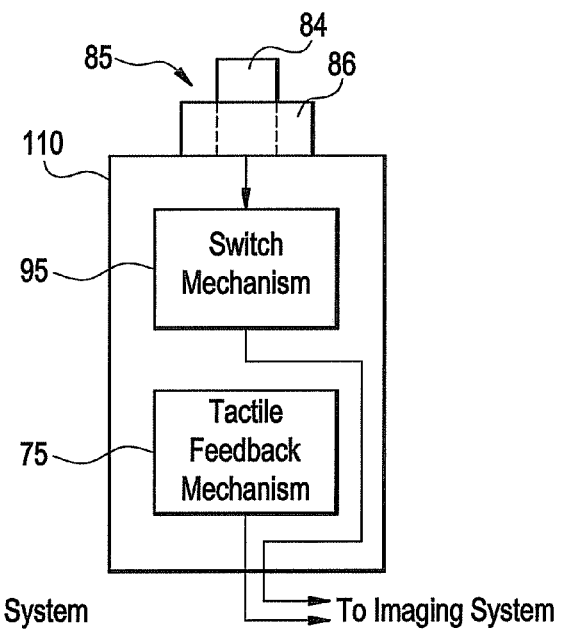
FIG. 3 depicts a pictorial schematic view of an x-ray handswitch in accordance with another embodiment of the invention.

Referring now to FIG. 3, another embodiment of the handswitch 110 is depicted. The handswitch 110 includes a tactile feedback mechanism 75, a two-stage nested push button 85, and a switch mechanism 95. In an embodiment, the two-stage nested push button 85, via the switch mechanism 95, is configured to initiate preparation of the x-ray system 100 for the x-ray exposure by pressing a first push button 84. In an embodiment, the two-stage nested push button 85, via the switch mechanism 95, is configured to initiate exposure of the x-ray system 100 by pressing a second push button 86. In an embodiment, the two-stage nested push button 85, is configured, via the switch mechanism 95, to initiate preparation of the x-ray in response to the first push button 84 being depressed approximately one-half of its total travel length, so as to make the top surface of the first push button 84 co-planar to the top surface of the second push button 86, and to initiate the x-ray exposure in response to being depressed fully, or such that the top surface of the first push button 84 is below the top surface of the second push button 86.

Figure 4:
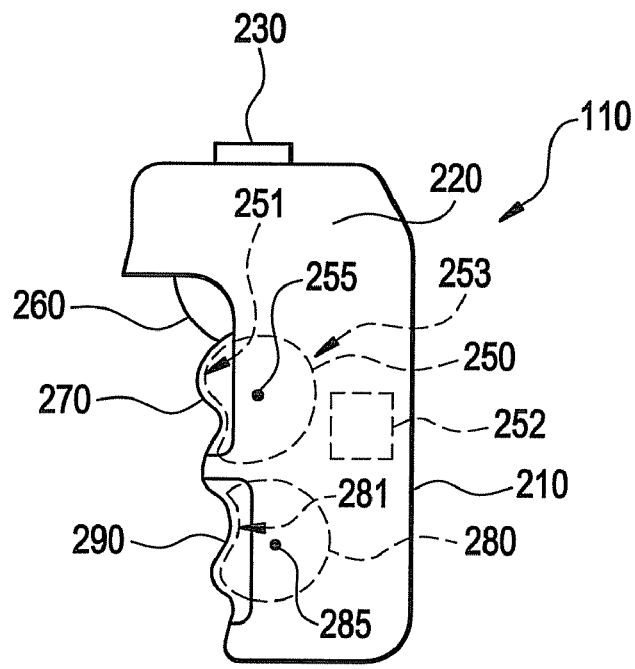
FIG. 4 depicts a side view of an exemplary x-ray handswitch in accordance with an embodiment of the invention.

Referring now to FIG. 4, an exemplary embodiment of the handswitch 110 is depicted. The handswitch 110 includes an exterior housing 210 that is suitably dimensioned so as to fit into the hand of the operator, an interior portion 220 housed within the exterior housing 210, and the exposure switch 230 disposed on the exterior housing 210 and configured to initiate the x-ray exposure, or provide the expose command. The handswitch 110 also includes a first tactile feedback mechanism 250, 252 disposed within the interior portion 220. In an embodiment, the first tactile feedback mechanism 250, 252 is in signal communication with the console 130 and is configured to indicate the transmission of x-rays by the x-ray system 100 to the operator of the x-ray system 100 via a feedback signal from the console 130 that is responsive to transmission of x-rays by the x-ray machine 120 of the x-ray system 100. In an embodiment, the first tactile feedback mechanism 250, 252 is configured to indicate transmission of x-rays by the x-ray machine via activation of the exposure switch 230, and accordingly, completion of the x-ray exposure to the operator of the x-ray system 100. In an embodiment, the handswitch 110 is configured to allow operation of the exposure switch 230 absent generation of an audible audio tone.

While an embodiment of the invention has been described transmitting x-rays via activation of the exposure switch disposed upon the handswitch, it will be appreciated that the scope of the invention is not so limited, and that the invention will also apply to tactile feedback mechanisms that are responsive to other causes of the transmission of x-rays by the x-ray system, such as the activation of an exposure switch disposed upon the x-ray console, and an unintended transmission of the x-rays, for example.

In an embodiment, the handswitch 110 further includes the prepare switch 260 disposed on the exterior housing 210. The prepare switch 260 is in signal communication with the console, and is configured to initiate preparation of the x-ray system 100 for the x-ray exposure. In an embodiment, a portion of the exterior housing 210 includes a first deformable surface 270, such as rubber, for example, or any other flexible material suitable for the purposes disclosed herein. In an embodiment, a portion of the exterior housing also includes a second deformable surface 290, such as rubber, for example, or any other flexible material suitable for the purposes disclosed herein. In an embodiment, the first and second deformable surfaces are flexible membranes.

While an embodiment of the invention has been described having a separate exposure switch and prepare switch, it will be appreciated that the scope of the invention is not so limited, and that the invention will also apply to handswitches that have other switch arrangements, such as a single, two-stage nested switch, to initiate preparation of the x-ray system 100 and to initiate the x-ray exposure, for example.

In an embodiment, the first tactile feedback mechanism 250 includes a low side 251 disposed adjacent to the first deformable surface 270, configured to match to an undeformed shape of the first deformable surface 270. In an embodiment, the first tactile feedback mechanism 250 also includes a high side 253. In an embodiment, the first tactile feedback mechanism 250 is configured to rotate around a pivot 255, which results in eccentric rotation of the first feedback mechanism 250.

Figure 5:
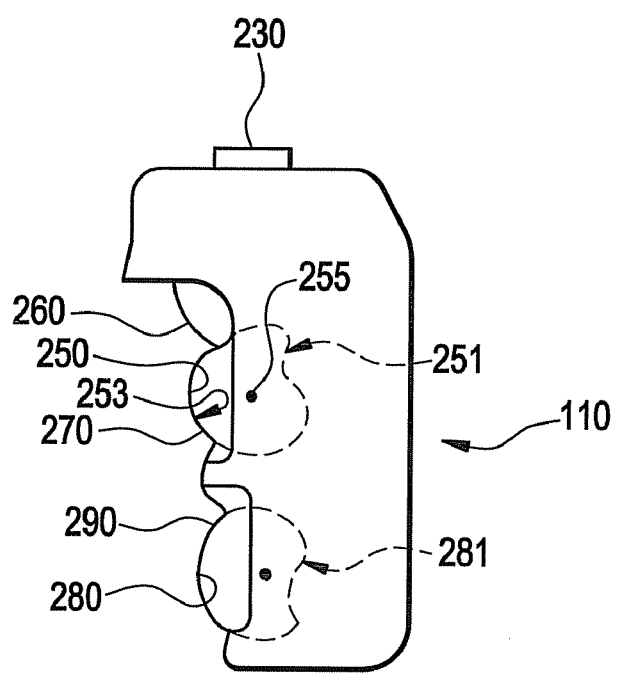
FIG. 5 depicts a side view of the exemplary x-ray handswitch of FIG. 4 depicting an alternate position of a feedback mechanism in accordance with an embodiment of the invention.

In an embodiment, the first tactile feedback mechanism 250 is configured to be responsive to activation of the exposure switch 230 and to cause deformation of the first deformable surface 270. Referring now to FIG. 5, it will be appreciated that in response to the activation of the exposure switch 230, the first tactile feedback mechanism 250 is depicted in a position that has been rotated about the pivot 255 approximately 180 degrees. In the position that has been rotated approximately 180 degrees, the high side 253 is adjacent to, and in contact with, the first deformable surface 270. In the position of the first tactile feedback mechanism 250 depicted in FIG. 5, the first tactile feedback mechanism 250 has caused the first deformable surface 270 to deform, and to conform to the shape of the high side 253 of the first tactile feedback mechanism 250. In an embodiment, this deformation, or change of shape, of the first deformable surface 270 will be observed and understood by the operator to indicate that an exposure has been completed. In an embodiment, the first tactile feedback mechanism 250 operates absent generation of an audio tone by the handswitch 110.

While an embodiment of the invention has been described having a surface capable of deformation, such as rubber, it will be appreciated that the scope of the invention is not so limited, and that the invention will also apply to other handswitch devices that may use alternate arrangements to provide a tactile feedback to the operator, such as a first surface made of other materials capable of deformation, such as latex or silicone, or a first surface that includes an aperture to allow direct exposure of the first tactile feedback mechanism, for example.

While an embodiment of the invention has been described having a tactile feedback mechanism that eccentrically rotates about a pivot, it will be appreciated that the scope of the invention is not so limited, and that the invention will also apply to other handswitch devices that may provide tactile feedback to the user in other ways, such as a tactile feedback device that translates in a linear motion from a first position to a second position, a tactile feedback device that has multiple sections to define a specific shape, and a tactile feedback device that may create other changes in the first surface to indicate activation of the exposure switch, such as temperature, for example. Further, while an embodiment of the invention has been described and depicted with a specific change in shape, it will be appreciated that the depicted change in shape is for illustration purposes only, and is not intended to limit the scope of the invention.

In an embodiment, in response to the activation of the exposure switch 230, the first tactile feedback mechanism 250 is configured to remain in the position depicted in FIG. 5, and therefore maintain the deformation of the first deformable surface 270. This will provide to the operator a clear indication of the transmission of x-rays by the x-ray system 100 via activation of the exposure switch 230, and therefore remove any uncertainty that proper completion of the exposure has occurred. In an embodiment, the first tactile feedback mechanism 250 is configured to return to the position as depicted in FIG. 4, wherein the low side 251 is adjacent the first deformable surface 270, in response to activation of the prepare switch 260. This will remove the deformation of the first deformable surface 270, and allow it to return to its original shape, depicted in FIG. 4.

While an embodiment of the invention has been described having a tactile feedback mechanism that transitions from a first position to a second position, it will be appreciated that the scope of the invention is not so limited, and that the invention will also apply to tactile feedback mechanisms that may provide dynamic feedback, such as a tactile feedback mechanism that is in motion to indicate a first status and is stationary to indicate a second status, for example.

In an embodiment, the handswitch 110 will also include a second tactile feedback mechanism 280 in signal communication with the console 130 and configured to indicate a preparation status of the x-ray system 100 to initiate the x-ray exposure. It will be appreciated that in an embodiment, the second tactile feedback 280 mechanism is configured to be responsive to the preparation status of the x-ray system 100 to initiate the x-ray exposure, and to cause deformation of the second deformable surface 290 in a manner as described above relating to the first tactile feedback mechanism 250 and the first deformable surface 270.

In an embodiment, in response to the x-ray system 100 being prepared to operate the x-ray exposure, the second tactile feedback mechanism 280 is configured to remain in the position depicted in FIG. 5, and therefore maintain deformation of the second deformable surface 290. This will provide to the operator a clear indication that the x-ray system 100 is prepared to operate the exposure, and therefore remove any uncertainty that proper preparation has been completed. In an embodiment, the second tactile feedback mechanism 280 is configured to return to the position as depicted in FIG. 4, wherein the low side 281 is adjacent the second deformable surface 290, in response to transmission of x-rays by the x-ray system 100 via activation of the exposure switch 230. Alternatively, the second tactile feedback mechanism 280 is configured to also return to the position as depicted in FIG. 4 in response to any change in the preparation status of the x-ray system 100 to operate the exposure. This return to the position depicted in FIG. 4 will remove the deformation of the second deformable surface 290, and allow it to return to its original shape.

In an embodiment, the first tactile feedback mechanism 252 is a vibrating mechanism 252 configured to vibrate in response to transmission of x-rays by the x-ray system 100 via activation of the exposure switch 230. In an embodiment, the vibrating mechanism 252 is configured to operate continuously for a specified period of time in response to transmission of x-rays by the x-ray system 100 via activation of the exposure switch 230. In another embodiment, the vibrating mechanism 252 is configured to operate in pulsed manner, wherein in response to transmission of x-rays by the x-ray system 100 via the activation of the exposure switch 230, a short duration of vibration is followed by a short duration absent vibration, and is repeated for a specified duration, or number of cycles. In yet another embodiment, the vibrating mechanism 252 is configured to operate in a coded manner, wherein the vibration begins with the beginning of the exposure and the vibration ends with the end of the exposure cycle, to indicate the start and end of the exposure cycle. In an embodiment, the vibrating mechanism is configured to operate in a coded manner to vary the duration and intensity of the vibration to indicate a parameter of the exposure, such as kilovolts-peak (kVp) or milliamps-second (mAs), for example.

As disclosed, some embodiments of the invention may include some of the following advantages: the ability to reduce environmental ambient noise level by eliminating the need to increase exposure tone volume; the ability to recognize exposure status independent of operator location; the ability to reduce uncertainty regarding exposure status; and the ability to ensure x-ray machine status of preparation.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

What is claimed is:

1. A handswitch configured to be held by an operator of an x-ray system configured for using handswitchable equipment to operate the x-ray system, the handswitch comprising:

an exterior housing so dimensioned as to fit into a hand of the operator, a portion of the exterior housing comprises a deformable surface;

an exposure switch disposed on the exterior housing and configured to initiate an x-ray exposure; and a tactile feedback mechanism configured to indicate, to the operator of the x-ray system, transmission of x-rays by the x-ray system, the tactile feedback mechanism being configured to be responsive to transmission of x-rays by the x-ray system and to cause tactile feedback at the deformable surface in response to activation of the exposure switch.

2. The handswitch of claim 1, wherein:
the handswitch is configured to allow operation absent generation of an audible tone.

3. The handswitch of claim 1, wherein:
the tactile feedback mechanism is configured to indicate, to the operator of the x-ray system, transmission of x-rays in response to activation of the exposure switch.

4. The handswitch of claim 1, wherein:
the tactile feedback mechanism comprises a vibrating mechanism configured to vibrate in response to transmission of x-rays by the x-ray system.

5. The handswitch of claim 4, wherein:
the vibrating mechanism is configured to operate continuously for a specified duration in response to transmission of x-rays by the x-ray system.

6. The handswitch of claim 4, wherein:
the vibrating mechanism is configured to operate in a pulsed manner for a specified duration in response to transmission of x-rays by the x-ray system.

7. The handswitch of claim 4, wherein:
the vibrating mechanism is configured to start vibrating at a beginning of the exposure, and to stop vibrating at an end of the exposure.

8. The handswitch of claim 4, wherein:
the vibrating mechanism is configured to vary at least one of vibration amplitude and vibration duration in response to a parameter of the x-ray exposure.

9. The handswitch of claim 1, wherein:
the tactile feedback mechanism is configured to cause a deformation of the deformable surface in response to activation of the exposure switch.

10. The handswitch of claim 9, further comprising:
a prepare switch disposed on the exterior housing, the prepare switch configured to initiate preparation of the x-ray system for the x-ray exposure.

11. The handswitch of claim 10, wherein:
in response to transmission of x-rays by the x-ray system, the tactile feedback mechanism is configured to maintain the deformation of the deformable surface; and
in response to activation of the prepare switch, the tactile feedback mechanism is configured remove the deformation of the deformable surface.

12. A handswitch configured to be held by an operator of an x-ray system configured for using handswitchable equipment to operate the x-ray system, the handswitch comprising:
an exterior housing so dimensioned as to fit into a hand of the operator;
an exposure switch disposed on the exterior housing and configured to initiate an x-ray exposure;
a first tactile feedback mechanism configured to indicate, to the operator of the x-ray system, transmission of x-rays by the x-ray system;
a prepare switch disposed on the exterior housing, the prepare switch configured to initiate preparation of the x-ray system for the x-ray exposure; and
a second tactile feedback mechanism configured to indicate a preparation status of the x-ray system to initiate the x-ray exposure;
wherein a portion of the exterior housing comprises a first deformable surface;
wherein the first tactile feedback mechanism is configured to be responsive to transmission of x-rays by the x-ray system and to cause a deformation of the first deformable surface in response to activation of the exposure switch;
wherein in response to transmission of x-rays by the x-ray system, the first tactile feedback mechanism is configured to maintain the deformation of the first deformable surface; and
wherein in response to activation of the prepare switch, the first tactile feedback mechanism is configured remove the deformation of the first deformable surface.

13. The handswitch of claim 12, wherein:
a portion of the exterior housing comprises a second deformable surface; and
the second tactile feedback mechanism is configured to be responsive to the preparation status of the x-ray system to initiate the x-ray exposure, and to cause a deformation of the second deformable surface in response to the x-ray system being prepared to initiate the x-ray exposure.

14. The handswitch of claim 13, wherein:
in response to the x-ray system being prepared to initiate the x-ray exposure, the second tactile feedback mechanism is configured to maintain the deformation of the second deformable surface.

15. An x-ray system to provide x-ray images of a subject, the system comprising:
an x-ray machine configured to transmit x-ray radiation and receive the transmitted x-ray radiation having passed through the subject;
an x-ray console in signal communication with the x-ray machine, the x-ray console configured to control the x-ray machine; and
a handswitch in signal communication with the x-ray console, the handswitch configured to be held by an operator of the x-ray system, the handswitch comprising:
an exterior housing so dimensioned as to fit into a hand of the operator, a portion of the exterior housing comprising a deformable surface;
an exposure switch disposed on the exterior housing and configured to initiate the x-ray transmission; and
a tactile feedback mechanism configured to indicate, to the operator of the x-ray system, transmission of x-rays by the x-ray system, the tactile feedback mechanism being configured to be responsive to transmission of x-rays by the x-ray system and to cause tactile feedback at the deformable surface in response to activation of the exposure switch.

16. The system of claim 15, wherein:
the handswitch is configured to allow operation absent generation of an audible tone.

17. The system of claim 15, wherein;
the first feedback mechanism comprises a vibrating mechanism configured to vibrate in response to transmission of x-rays by the x-ray system.

18. The system of claim 17, wherein:
the vibrating mechanism is configured to start vibrating at a beginning of the exposure, and to stop vibrating at an end of the exposure.

19. The system of claim 17, wherein:
the vibrating mechanism is configured to vary at least one of vibration amplitude and vibration duration in response to a parameter of the x-ray exposure.

20. The system of claim 15, wherein:
the tactile feedback mechanism is configured to cause a deformation of the first deformable surface in response to activation of the exposure switch.

* * * * *